(12) United States Patent
Altmann et al.

(10) Patent No.: US 11,911,196 B2
(45) Date of Patent: Feb. 27, 2024

(54) SEEING THROUGH MUCUS IN AN ENT PROCEDURE

(71) Applicant: BIOSENSE WEBSTER (ISRAEL) LTD., Yokneam (IL)

(72) Inventors: Andres Claudio Altmann, Haifa (IL); Vadim Gliner, Haifa (IL); Ram Bernard Mayer, Raanana (IL)

(73) Assignee: Biosense Webster (Israel) Ltd., Yokneam (IL)

(*) Notice: Subject to any disclaimer, the term of this patent is extended or adjusted under 35 U.S.C. 154(b) by 0 days.

(21) Appl. No.: 17/713,362

(22) Filed: Apr. 5, 2022

(65) Prior Publication Data

US 2022/0225951 A1    Jul. 21, 2022

Related U.S. Application Data

(62) Division of application No. 16/841,745, filed on Apr. 7, 2020, now abandoned, which is a division of
(Continued)

(51) Int. Cl.
*A61B 6/12* (2006.01)
*A61B 6/03* (2006.01)
(Continued)

(52) U.S. Cl.
CPC ............ *A61B 6/12* (2013.01); *A61B 5/062* (2013.01); *A61B 6/032* (2013.01); *A61B 6/461* (2013.01);
(Continued)

(58) Field of Classification Search
CPC ............ A61B 2090/3966; A61B 34/20; A61B 2034/2051; A61B 5/061; A61B 90/39;
(Continued)

(56) References Cited

U.S. PATENT DOCUMENTS 7,630,529 B2    12/2009  Zalis
2005/0107679 A1  5/2005  Geiger et al.
(Continued)

FOREIGN PATENT DOCUMENTS

WO    WO2005008591    1/2005
WO    WO2008/121578   10/2008
WO    WO2016083275    6/2016

OTHER PUBLICATIONS

European Search Report dated Jun. 14, 2018 from corresponding European Patent Application No. 18151661.8.

*Primary Examiner* — Deborah L Malamud

(57) ABSTRACT

A method for radiographic imaging of a body cavity includes imaging the body cavity using computerized tomography (CT) to form a CT image, registering a tracking system with the CT image, inserting into the body cavity a guidewire, including a position sensor, operating in the tracking system, attached to a distal end of the guidewire, in response to signals from the position sensor acquired by the tracking system, displaying a position of the distal end of the guidewire on the CT image. The method further includes assigning voxels within a predefined imaging volume relative to the distal end and having a radiodensity less than a predetermined threshold to have a uniform radiodensity of a predefined default value, incorporating the voxels with the assigned predefined default value into the CT image so as to form an updated CT image, and displaying the updated CT image.

9 Claims, 6 Drawing Sheets

Related U.S. Application Data application No. 15/407,060, filed on Jan. 16, 2017, now Pat. No. 10,631,798.

(51) Int. Cl.

| | | |
|---|---|---|
| *A61B 5/06* | (2006.01) | |
| *A61B 6/00* | (2006.01) | |
| *A61B 90/00* | (2016.01) | |
| *G06T 11/00* | (2006.01) | |
| *A61B 34/20* | (2016.01) | |

(52) U.S. Cl.
CPC .......... *A61B 6/5205* (2013.01); *A61B 6/5252* (2013.01); *A61B 6/547* (2013.01); *A61B 90/37* (2016.02); *G06T 11/006* (2013.01); *A61B 2034/2046* (2016.02)

(58) Field of Classification Search
CPC ............ A61B 2034/2065; A61B 6/032; A61B 2034/107; A61B 2034/2055; A61B 5/742; A61B 6/463; A61B 6/5223; A61B 2090/3762; A61B 5/065; A61B 5/7425; A61B 8/483; A61B 5/0073; A61B 2090/364; A61B 6/5247; A61B 2090/367; A61B 6/037; A61B 6/461; A61B 6/466; A61B 6/547; A61B 90/361; A61B 2576/00; A61B 5/1128; A61B 6/02; A61B 6/03; A61B 1/00045; A61B 5/00; A61B 5/0013; A61B 5/0077; A61B 5/05; A61B 5/743; A61B 5/5211; A61B 8/466; A61B 90/36; G06T 7/0012; G06T 19/00; G06T 1/00; G06T 2210/41; G06T 2210/10072; G06T 2207/20101; G06T 19/003; G06T 2207/10081; G06T 7/136; G06T 11/005; G06T 17/00; G06T 1/0007; G06T 2200/04; G06T 2200/08; G06T 2207/30004; A61M 25/0108; A61M 25/09; A61M 2205/3303; A61M 2205/3317; A61M 1/0025; A61N 2005/1061; G16H 30/40
See application file for complete search history.

(56) References Cited

U.S. PATENT DOCUMENTS

| | | |
|---|---|---|
| 2008/0008367 A1 | 1/2008 | Franaszek et al. |
| 2013/0004044 A1 | 1/2013 | Ross et al. |
| 2014/0276002 A1 | 9/2014 | West |
| 2014/0330115 A1 | 11/2014 | Schildraut et al. |

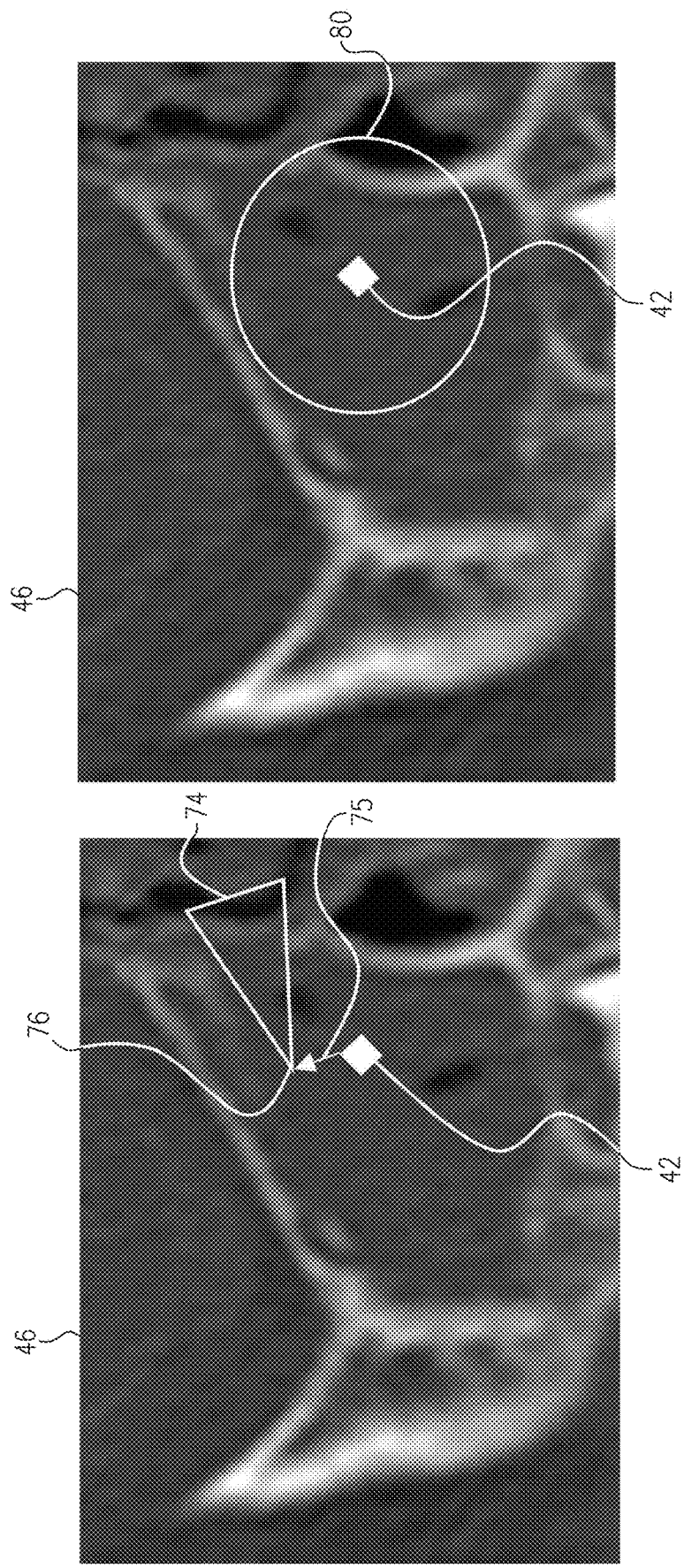

SEEING THROUGH MUCUS IN AN ENT PROCEDURE

CROSS-REFERENCE TO RELATED APPLICATION

This application is a divisional of U.S. patent application Ser. No. 16/841,745, filed on Apr. 7, 2020, which is a divisional of U.S. patent application Ser. No. 15/407,060, filed on Jan. 16, 2017, now U.S. Pat. No. 10,631,798, priority of which is hereby claimed.

FIELD OF THE INVENTION

The present invention relates generally to medical imaging, and particularly to imaging using X-rays.

BACKGROUND

In medical computerized tomography (CT), a large number of X-ray images are taken from different angles of a part of the body of a patient. Using the mathematical procedure of tomographic reconstruction, the X-ray images are processed and combined to yield cross-sectional images of the part of the body, providing a non-invasive three-dimensional (3D) image of the internal structure of the imaged part.

U.S. Pat. No. 7,630,529, which is incorporated herein by reference, describes a system for performing a virtual colonoscopy that is stated to include a system for generating digital images, a storage device for storing the digital images, a digital bowel subtraction processor coupled to receive images of a colon from the storage device and for removing the contents of the colon from the image and an automated polyp detection processor coupled to receive images of a colon from the storage device and for detecting polyps in the colon image.

U.S. Patent application 2014/0330115, which is incorporated herein by reference, describes a method for displaying a paranasal sinus region of a patient that is executed at least in part on a computer. The method is stated to include acquiring volume image data of the paranasal sinus region of the patient, identifying one or more airways within the paranasal sinus region from the volume image data, displaying the at least one or more airways, and highlighting one or more portions of the displayed airways that are constricted below a predetermined value.

U.S. Patent application 2013/0004044, which is incorporated herein by reference, describes a voxel-based technique that is provided for performing quantitative imaging and analysis of tissue image data. Serial image data is collected for tissue of interest at different states of the issue. The collected image data may be deformably registered, after which the registered image data is analyzed on a voxel-by-voxel basis, thereby retaining spatial information for the analysis. Various thresholds are applied to the registered tissue data to identify a tissue condition or state, such as classifying chronic obstructive pulmonary disease by disease phenotype in lung tissue, for example.

U.S. Patent application 2008/0008367, which is incorporated herein by reference, describes how an image of an anatomical structure can be analyzed to determine an enclosing three-dimensional boundary when the anatomical structure is filled with two substances, such as air and a fluid. Various techniques can be used to determine the enclosing boundary including: analyzing the virtual structure to segment the structure into air and fluid pockets, determining if there are multiple fluid pockets whose surface touches a single air-fluid boundary, determining a separate threshold for respective fluid pockets, resegmenting the virtual anatomical structure using the separate threshold for different fluid pockets, forming a hierarchical pocket tree which represents the relationship between the fluid and air pockets, pruning the pocket tree based on various criteria which corresponds to deleting those pruned portions from the virtual anatomical structure, and resegmenting the remaining virtual anatomical structure using one or more of fuzzy connectedness, two-dimensional gap filling, and level set segmentation.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY

Embodiments of the present invention that are described hereinbelow provide an improved method for local radiographic imaging within body cavities.

There is therefore provided, in accordance with an embodiment of the present invention, a method for radiographic imaging of a body cavity, including imaging the body cavity using computerized tomography (CT) to form a CT image, registering a tracking system with the CT image, inserting into the body cavity a guidewire, including a position sensor, operating in the tracking system, attached to a distal end of the guidewire, in response to signals from the position sensor acquired by the tracking system, displaying a position of the distal end of the guidewire on the CT image. The method further includes assigning voxels within a predefined imaging volume relative to the distal end and having a radiodensity less than a predetermined threshold to have a uniform radiodensity of a predefined default value, incorporating the voxels with the assigned predefined default value into the CT image so as to form an updated CT image, and displaying the updated CT image.

In another embodiment the method includes a predefined imaging volume which includes a conical volume having an apex offset from the distal end by a predefined vector.

In yet another embodiment the method includes a predefined imaging volume which includes a sphere having a center offset from the distal end by a predefined vector.

In some embodiments the method includes a predetermined threshold having the radiodensity of mucus or the radiodensity of a selected body tissue.

In an embodiment the method includes a predefined default value having the radiodensity of air.

In a further embodiment the method includes radiographic imaging of a the body cavity including a nasal sinus.

There is also provided, in accordance with an embodiment of the present invention, an apparatus for radiographic imaging of a body cavity, including a guidewire inserted in the body cavity, the guidewire including a position sensor, operating in a tracking system, at its distal end, and a display screen. The apparatus further includes a processor coupled to the position sensor and to the display screen, configured to store and display a CT image of the body cavity, to register the tracking system with the CT image, to track a position of the distal end, to display on the display screen the tracked position of the distal end superimposed on the CT image, to assign voxels within a predefined imaging volume relative to the distal end and having a radiodensity less than a predetermined threshold to have a uniform radiodensity of a predefined default value, to incorporate the voxels with the assigned predefined default value into the CT image so as to form an updated CT image, and to display the updated CT image on the display screen.

In another embodiment the predefined imaging volume includes a conical volume having an apex offset from the distal end by a predefined vector. Alternatively, the predefined imaging volume includes a sphere having a center offset from the distal end by a predefined vector.

In yet another embodiment the predetermined threshold includes a radiodensity of mucus. Alternatively, the predetermined threshold includes a radiodensity of a selected bodily tissue.

In an embodiment the predefined default value includes radiodensity of air.

In a further embodiment the body cavity includes a nasal sinus.

The present invention will be more fully understood from the following detailed description of the embodiments thereof, taken together with the drawings in which:

BRIEF DESCRIPTION OF THE DRAWINGS

FIG. 6 shows a spatially offset conical imaging volume, according to an embodiment of the present invention;

FIG. 7 shows a definition of a spherical imaging volume, according to an embodiment of the present invention.

DETAILED DESCRIPTION OF EMBODIMENTS

Overview

Radiographic imaging of body cavities is commonly performed using computerized tomography (CT). The quality of the obtained radiographic image is often reduced due to the presence of substances other than air in the cavity, and an example of such a situation is CT imaging of the nasal sinuses, when a nasal sinus is filled with mucus instead of air. Although in the following the effect of mucus on the imaging of nasal sinuses is described as an example, it will be appreciated that the embodiments of the present invention comprise CT imaging of other body cavities with substances other than air therein.

Embodiments of the present invention that are described herein solve this problem by generating an image of a cavity as if only air fills the cavity.

In an embodiment of the present invention, a patient is scanned, in advance of a medical procedure, in a CT imaging device, generating a CT image comprising a body cavity of the patient. In a subsequent medical procedure, a guidewire with a position sensor at its distal end is inserted into the patient's body cavity, the position sensor enabling tracking of the position of the distal end. Using known registration procedures, a tracking system wherein the position sensor operates has been registered in advance with the CT image. The registration enables the tracked position of the distal end to be displayed on the CT image of the patient's body cavity.

The radiodensities of the voxels in a predefined imaging volume, relative to the distal end of the guidewire, are compared to a predetermined radiodensity threshold. Voxels in the predefined imaging volume having a radiodensity that is less than a predetermined threshold, are assigned a predefined default value. The voxels having the radiodensity that has been assigned with the predefined default value are incorporated into the CT image to form an updated CT image, and this updated CT image is displayed.

System Description

Figure 1:
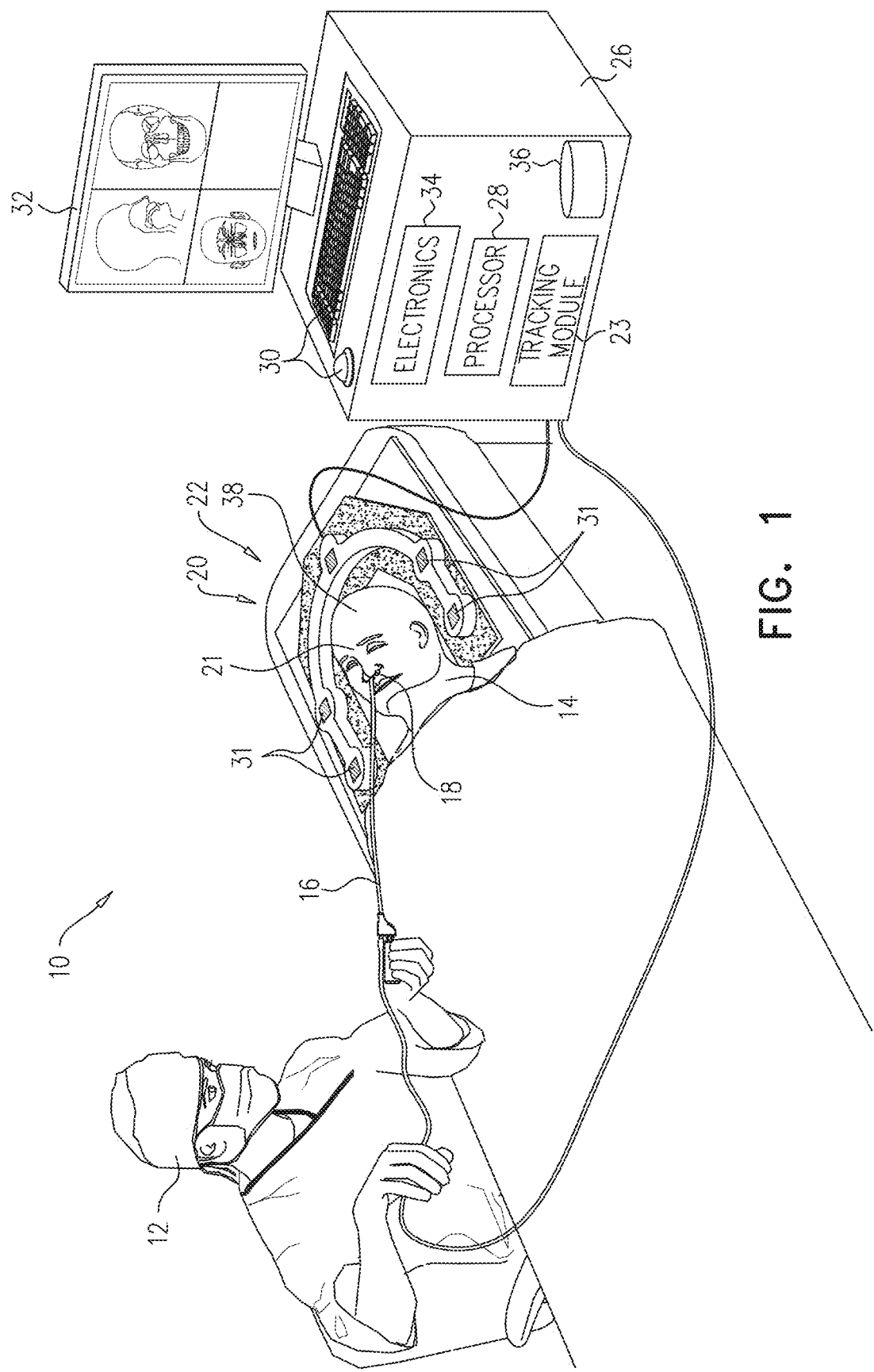
FIG. 1 is a schematic illustration of a medical procedure, according to an embodiment of the present invention.

FIG. 1 is a schematic illustration of a medical procedure using apparatus 10, according to an embodiment of the present invention. The procedure is performed by a surgeon 12, and, by way of example, the procedure in the description hereinbelow is assumed to comprise inserting a guidewire into the nasal sinus of a patient 14 for a medical procedure within the nasal sinus. However, it will be understood that embodiments of the present invention are not just applicable to this specific procedure, and may include substantially any procedure on biological tissue.

Surgeon 12 inserts a guidewire 16 into a nostril 18 of patient 14, so that a distal end 20 of the guidewire enters a nasal sinus cavity 21 of the patient. Distal end 20 comprises position sensor 22. A proximal end 24 of guidewire 16 is coupled to a console 26 of apparatus 10.

Apparatus 10 is controlled by a processor 28, which is located in console 26. Console 26 comprises controls 30, which are used by surgeon 12 to communicate with the processor. During the procedure, processor 28 tracks a location and an orientation of distal end 20 of the catheter, using any method known in the art. For example, processor 28 may use a magnetic tracking method, wherein magnetic transmitters 31, external to patient 14, generate signals in coils located in position sensor 22. The signals from the sensor coils are connected to console 26 and further to magnetic tracking module 23 and are analyzed by the magnetic tracking module communicating with processor 28. The Carto® system produced by Biosense Webster, of Diamond Bar, CA, uses such a tracking method.

The software for processor 28 may be downloaded to the processor in electronic form, over a network, for example. Alternatively or additionally, the software may be provided on non-transitory tangible media, such as optical, magnetic, or electronic storage media. Processor 28 is coupled to a display screen 32.

In order to operate apparatus 10, processor 28 communicates with electronics 34, which incorporates a magnetic tracking module 23 and other modules used by the processor to operate the apparatus. For simplicity, such other modules, which may comprise hardware as well as software elements, are not illustrated in FIG. 1. Proximal end 24 of guidewire 16, coupled to console 26, is further coupled to magnetic tracking module 23 so that the module is able to use the signals generated by sensor 22 for position tracking.

Processor 28 further communicates with a memory 36, which stores data required for operating apparatus 10. The data comprises CT images of a head 38 of patient 14.

Figure 2:
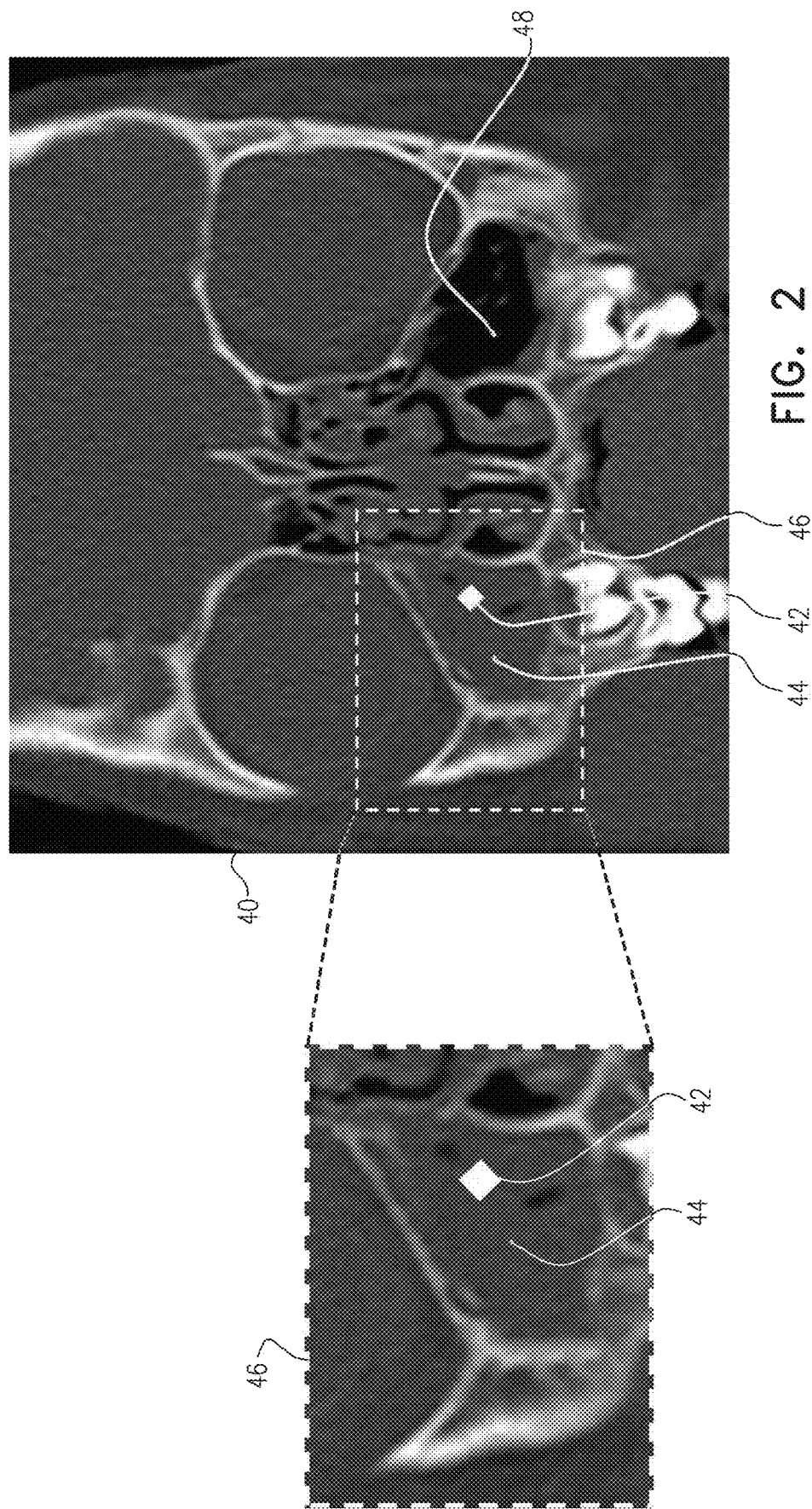
FIG. 2 shows a frontal section of a CT image of the head of a patient, according to an embodiment of the present invention.

FIG. 2 shows a frontal section of a CT image 40 of head 38 of patient 14, according to an embodiment of the present invention. Using known registration procedures, the magnetic tracking system is registered with the CT imaging system. Utilizing the registration together with the detected position of distal end 20, the position is superimposed as a fiducial mark 42 on CT image 40. In CT image 40, surgeon 12 is assumed to have inserted distal end 20 of guidewire 16 into a right maxillary sinus 44 of patient 14, as shown by the position of fiducial mark 42 within CT image 40. A CT image 46, which is an enlarged part of CT image 40, is shown to the right of CT image 40.

A comparison of the image of right maxillary sinus 44 with the image of a left maxillary sinus 48 in CT image 40 shows that the image of right maxillary sinus 44 is lighter than the image of left maxillary sinus 48. This difference indicates a different radiographic density of the two maxillary sinuses 44 and 48, respectively. The different radiographic density, in turn, is due to the fact that right maxillary sinus 44 is filled with mucus.

The radiodensity is conventionally expressed in Hounsfield units (HU), and the radiodensity of mucus is typically between −100 HU and +100 HU. Left maxillary sinus 48 is filled with air, with a radiographic density of −1000 HU. As is described with reference to the flowchart of FIG. 3, in an embodiment of the present invention, in further processing of CT image 46 in FIG. 2, the upper radiodensity of mucus, +100 HU, is selected as a radiodensity threshold for the re-assignment of voxel radiodensities, and the radiodensity of air, −1000 HU, is selected as the default radiodensity for the assigned value.

Figure 3:
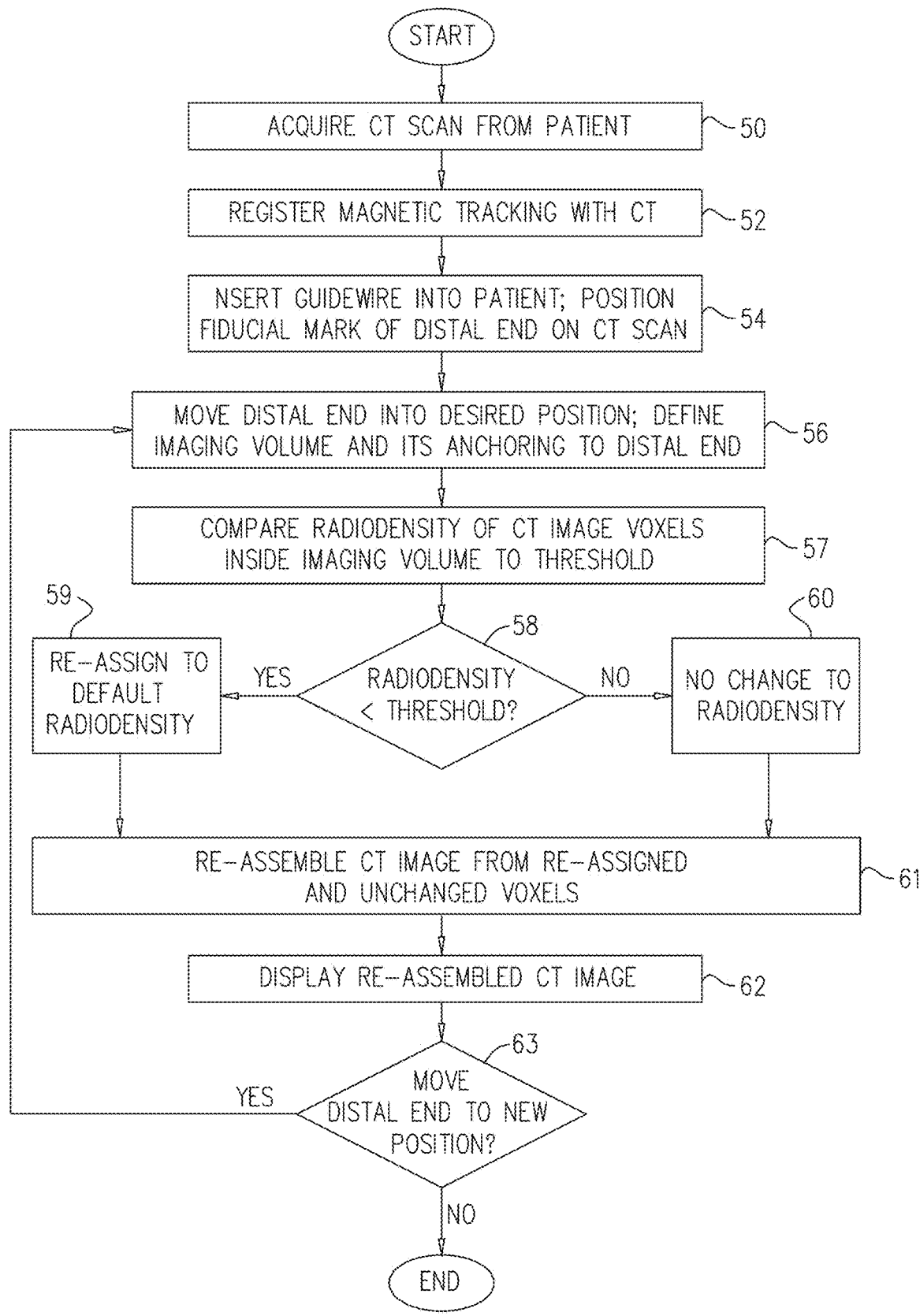
FIG. 3 is a flowchart of steps that are implemented during the medical procedure, as relating to imaging, according to an embodiment of the present invention.

FIG. 3 is a flowchart of steps that are implemented during the medical procedure, as relating to imaging, according to an embodiment of the present invention. In a CT scan step 50, head 38 of patient 14 is scanned by computerized tomography (CT), herein by way of example assumed to be fluoroscopic CT, and the CT data from the scan is acquired by processor 28 and stored in memory 36. The CT scan of patient 14 may be performed independently of the implementation of the remaining steps of the flowchart, which correspond to a nasal sinus procedure. Typically, CT scan step 50 may be performed a number of days before the following steps of the procedure.

In an initial procedure step 52, the magnetic tracking system, comprising magnetic transmitters 31, position sensor 22, and magnetic tracking module 23, is registered with the CT imaging system. The registration may be implemented by any method known in the art. In step 52, surgeon 12 defines a level of the preset radiodensity threshold, and the level is herein, by way of example, assumed to be +100 HU. Also in step 52, the surgeon defines a level for the default radiodensity, and this level is herein, by way of example, assumed to be that of air, i.e., 1000 HU.

In an insertion step 54, surgeon 12 inserts guidewire 16 into nostril 18 of patient 14, so that distal end 20 of the guidewire enters nasal sinus cavity 21 of the patient. Utilizing the registration between the magnetic tracking system and the CT imaging system, together with the detected position of distal end 20, this position is superimposed as fiducial mark 42 on CT image 46, as is illustrated in FIG. 2.

In a defining step 56, surgeon 12 moves distal end 20 into a desired position, utilizing fiducial mark 42 on CT image 46 for guidance. In defining step 56, surgeon 12 further defines an imaging volume by its shape, size, and anchoring to distal end 20, as is described in more detail with respect to FIGS. 4 and 6-8.

Figure 4:
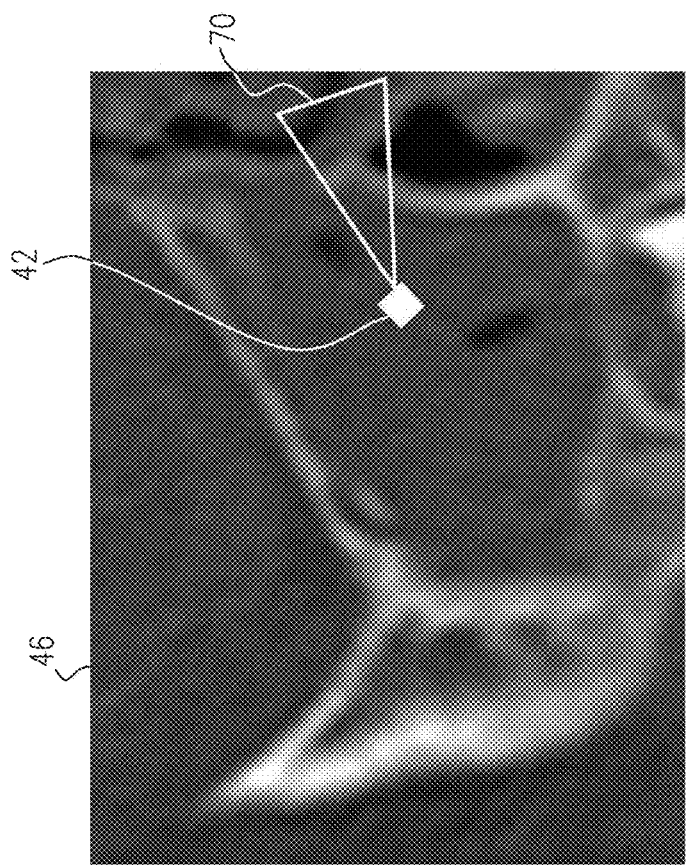
FIG. 4 shows a definition of a conical imaging volume anchored to distal end of the guidewire, according to an embodiment of the present invention.

FIG. 4 shows, with reference to FIGS. 1-2, in CT image 46 a definition of a conical imaging volume 70 anchored to distal end 20 of guidewire 16, according to an embodiment of the present invention. Surgeon 12 defines the anchoring of conical imaging volume 70 by defining the apex of the conical imaging volume to coincide with fiducial mark 42. Surgeon 12 further defines an apex angle of conical imaging volume 70, and a typical angle is 60°, although the surgeon may select any other convenient value for the angle. Typically, processor 28 defines a length of conical imaging volume 70.

FIG. 6 shows a spatially offset conical imaging volume 74, according to an embodiment of the present invention. Offset conical imaging volume 74 has been defined by surgeon similarly to conical imaging volume 70 with respect to FIG. 4, but the surgeon has additionally defined an offset vector 75 separating an apex 76 from fiducial mark 42.

FIG. 7 shows a definition of a spherical imaging volume 80, according to an embodiment of the present invention. Surgeon 12 has defined a radius of spherical imaging volume 80, and has also defined the volume center to coincide with fiducial mark 42. A typical radius for volume 80 is 5 mm, but the surgeon may select any other convenient value for the radius.

Figure 8:
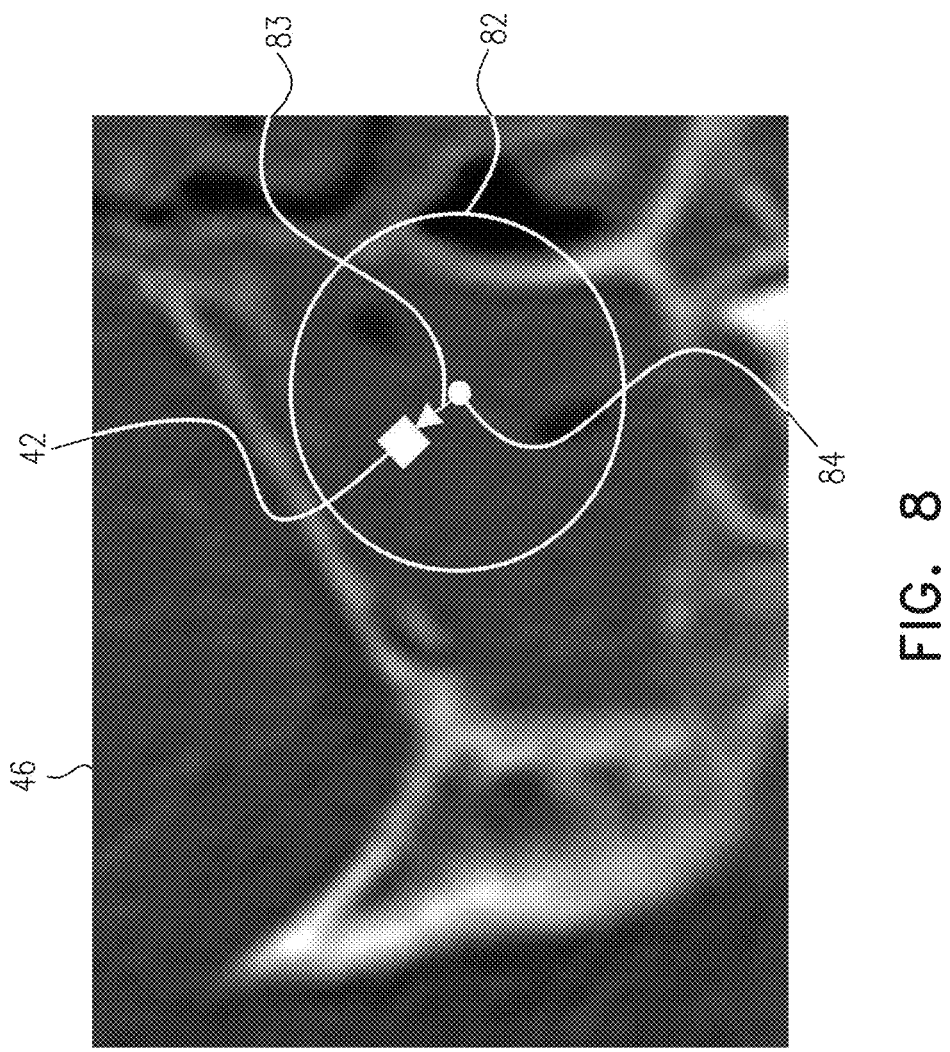
FIG. 8 shows a spatially offset spherical imaging volume, according to an embodiment of the present invention.

FIG. 8 shows a spatially offset spherical imaging volume 82, according to an embodiment of the present invention. Offset spherical imaging volume 82 has been defined by surgeon 12 similarly to spherical imaging volume 80 in FIG. 7, but the surgeon has additionally defined an offset vector 83 separating a center 84 of spherical imaging volume 82 from fiducial mark 42.

In the examples described above defining the anchoring of the imaging volume to fiducial mark 42, surgeon 12 has used finite (non-zero) offset vectors 75, 83 in FIG. 6 and in FIG. 8. However, it will be understood that in embodiments of the present invention offset vectors comprise both finite (non-zero) and zero-length vectors.

Returning to the flowchart in a comparison step 57, processor 28 compares the radiodensity of each voxel within the imaging volume defined in step 56 to the preset radiodensity threshold defined in step 52, and passes each voxel within the imaging volume on to a decision step 58. With respect to FIGS. 4 and 6-8, the imaging volume whose voxels are processed in comparison step 57 and decision step 58 are conical imaging volume 70 (FIG. 4), offset conical imaging volume 74 (FIG. 6), spherical imaging volume 80 (FIG. 7), and offset spherical imaging volume 82 (FIG. 8).

In decision step 58, the following two alternative decisions are taken: if the radiodensity of the voxel under comparison is less than the predetermined threshold, which surgeon 12 has in step 52 defined as +100 HU, processor 28 directs the handling to a re-assignment step 59, whereas if the radiodensity of the voxel under comparison is not less than the predetermined threshold of +100 HU, processor 28 directs the handling to a no-change step 60.

In re-assignment step 59, the voxel that processor 28 has passed to the re-assignment step is re-assigned by the processor a radiodensity value equal to the predefined default radiodensity, which is set in step 52, and is herein assumed to be that of air, −1000 HU. After the re-assignment, processor 28 passes the re-assigned voxel to a re-assembly step 61.

In no-change step 60, the voxel that processor 28 has passed to the no-change step is further passed on by the processor to re-assembly step 61, leaving the radiodensity of the voxel intact.

Re-assembly step 61 receives the voxels of the imaging volume from re-assignment step 59 and no-change step 60 with their re-assigned or unchanged values, respectively. In re-assembly step 61 processor 28 re-assembles the portion of CT image 46 within the imaging volume from the received voxels, with the portion of CT image 46 outside the imaging volume remaining intact.

In a display step 62, processor 28 displays CT image 46 with re-assembled voxels on display 32.

Figure 5:
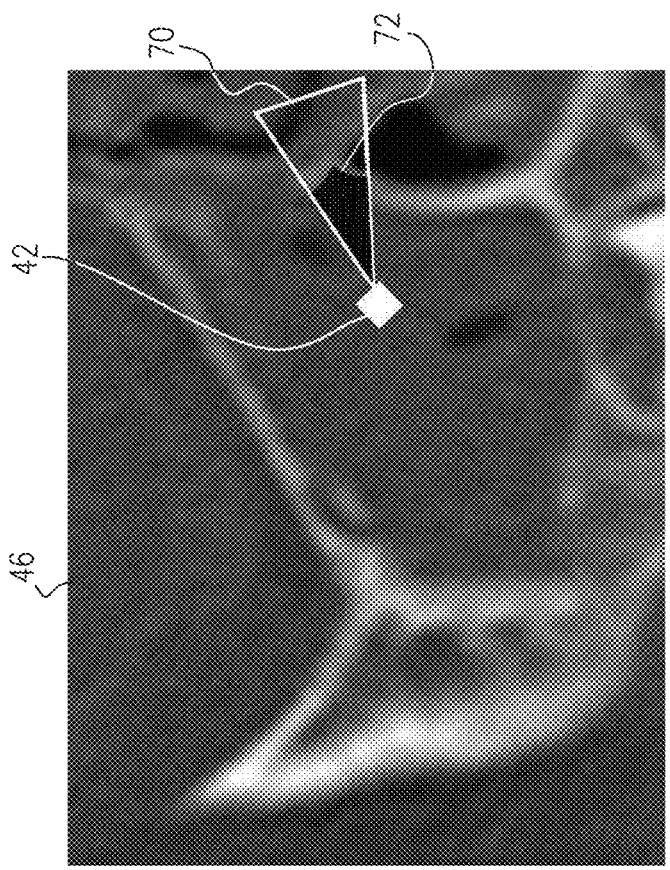
FIG. 5 shows an enlarged area of a CT image after re-assignment of voxels within a conical imaging volume, and displaying the image with re-assigned voxels, according to an embodiment of the present invention.

FIG. 5 illustrates an example of a CT image 46' with re-assembled voxels, according to an embodiment of the present invention. FIG. 5 shows the change in the image of FIG. 4, after display step 62 has been implemented. The voxels within an area 72 within conical imaging volume 70 have an original radiographic density less than +100 HU, and processor 28 has consequently assigned them the radiographic density of air, −1000 HU, using steps 57, 58 and 59. CT image 46' illustrates the re-assignment of the radiodensity of the voxels in area 72, making them radiographically transparent and increasing the contrast and clarity of the features within conical imaging volume 70, as compared to CT image 46 in FIG. 4.

Similarly to the re-assignment for conical imaging volume 70 and with respect to FIGS. 6-8, processor 28 re-assigns the radiodensity of the voxels within offset conical imaging volume 74 (FIG. 6), spherical imaging volume 80 (FIG. 7), and offset spherical imaging volume 82 (FIG. 8) in the same fashion as that for conical imaging volume 70 in FIG. 5. The images displayed after re-assignment of the voxels (not shown here) show mucus as air, increasing the contrast and clarity of the features within these imaging volumes.

Returning to the flowchart, in a decision step 63, surgeon 12 decides whether he/she wants to move guidewire 16 to a new position within nasal sinus cavity 21. If he/she desires to move guidewire 16, he/she may at defining step 56 either re-define the imaging volume, or alternatively leave it as previously defined. The latter alternative corresponds to moving distal end 20 within nasal sinus cavity 21 and imaging in a scanning fashion. Scanning distal end 20 within nasal sinus cavity 21 has the effect of increasing the contrast and clarity of the features within the scanned imaging volume.

If surgeon 12 decides not to move guidewire 16 further, the procedure ends.

The description above has assumed the predetermined threshold to be that of mucus, but it will be understood that other threshold values may be used. For example, surgeon 12 may choose the radiodensity threshold to be the radiodensity of a selected tissue or bone, which will have the effect of making the tissue or bone radiographically transparent within the imaging volume defined by surgeon 12 in defining step 56.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An apparatus for radiographic imaging of a body cavity, comprising:
    a guidewire configured for being inserted in the body cavity, the guidewire comprising a position sensor, operating in a tracking system, at a distal end of the guidewire, wherein the body cavity comprises a nasal sinus;
    a display screen;
    a processor coupled to the position sensor and to the display screen, configured to:
    store and display a CT image of the body cavity;
    register the tracking system with the CT image;
    track a position of the distal end;
    display on the display screen the tracked position of the distal end superimposed on the CT image;
    assign voxels within a predefined imaging volume relative to the distal end and having a radiodensity less than a predetermined threshold to have a uniform radiodensity of a predefined default value;
    incorporate the voxels with the assigned predefined default value into the CT image so as to form an updated CT image; and
    display the updated CT image on the display screen.

2. The apparatus for radiographic imaging according to claim 1, wherein the predefined imaging volume comprises a conical volume having an apex offset from the distal end by a predefined vector.

3. The apparatus for radiographic imaging according to claim 1, wherein the predefined imaging volume comprises a sphere having a center offset from the distal end by a predefined vector.

4. The apparatus for radiographic imaging according to claim 1, wherein the predetermined threshold comprises a radiodensity of mucus.

5. The apparatus for radiographic imaging according to claim 1, wherein the predetermined threshold comprises a radiodensity of a selected bodily tissue.

6. The apparatus for radiographic imaging according to claim 1, wherein the predefined default value comprises radiodensity of air.

7. An apparatus for radiographic imaging of a body cavity, comprising:
    a guidewire configured for being inserted in the body cavity, the guidewire comprising a position sensor, operating in a tracking system, at a distal end of the guidewire;
    a display screen;
    a processor coupled to the position sensor and to the display screen, configured to:
    store and display a CT image of the body cavity;
    register the tracking system with the CT image;
    track a position of the distal end;
    display on the display screen the tracked position of the distal end superimposed on the CT image;
    assign voxels within a predefined imaging volume relative to the distal end and having a radiodensity less than a predetermined threshold to have a uniform radiodensity of a predefined default value, wherein the predetermined threshold comprises a radiodensity of mucus;
    incorporate the voxels with the assigned predefined default value into the CT image so as to form an updated CT image; and
    display the updated CT image on the display screen.

8. The apparatus for radiographic imaging according to claim 7, wherein the predefined imaging volume comprises a conical volume having an apex offset from the distal end by a predefined vector.

9. The apparatus for radiographic imaging according to claim 7, wherein the predefined imaging volume comprises a sphere having a center offset from the distal end by a predefined vector.

* * * * *